United States Patent
Eisinger et al.

(10) Patent No.: US 11,627,966 B2
(45) Date of Patent: Apr. 18, 2023

(54) SURGICAL STAPLING DEVICE

(71) Applicant: Covidien LP, Mansfield, MA (US)

(72) Inventors: Joseph T. Eisinger, Northford, CT (US); David E. Valentine, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/394,825

(22) Filed: Aug. 5, 2021

(65) Prior Publication Data

US 2022/0061850 A1 Mar. 3, 2022

Related U.S. Application Data (60) Provisional application No. 63/070,520, filed on Aug. 26, 2020.

(51) Int. Cl.
| | |
|---|---|
| *A61B 17/064* | (2006.01) |
| *A61B 17/115* | (2006.01) |
| *A61B 17/00* | (2006.01) |
| *A61B 17/072* | (2006.01) |

(52) U.S. Cl.
CPC ... *A61B 17/1155* (2013.01); *A61B 2017/0046* (2013.01); *A61B 2017/00486* (2013.01); *A61B 2017/00831* (2013.01); *A61B 2017/07257* (2013.01); *A61B 2017/07271* (2013.01)

(58) Field of Classification Search
CPC .... A61B 2017/00017; A61B 17/00398; A61B 17/1155
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Apr. 12, 2022, issued in corresponding EP Appln. No. 21192985, 11 pages.

*Primary Examiner* — Eyamindae C Jallow
(74) *Attorney, Agent, or Firm* — Carter, DeLuca & Farrell LLP (57) ABSTRACT

A reusable surgical device includes a housing or body that supports one or more thermal energy storage members that retain or store heat during a cleaning and sterilization process. The stored heat functions to evaporate water that remains within the body or housing of the surgical device after the cleaning and sterilization process is completed to minimize any likelihood of infection of a patient or damage to electronics within the surgical device that may result or occur due to the presence of the water within the surgical device.

20 Claims, 5 Drawing Sheets

(56) References Cited

U.S. PATENT DOCUMENTS

| | | |
|---|---|---|
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |

(56) References Cited

U.S. PATENT DOCUMENTS

| | | |
|---|---|---|
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |

(56) References Cited

U.S. PATENT DOCUMENTS

| | | |
|---|---|---|
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |
| 9,364,229 B2 | 6/2016 | D'Agostino et al. |

(56) References Cited

U.S. PATENT DOCUMENTS

| | | |
|---|---|---|
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0253329 A1 | 10/2012 | Zemlok et al. |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0284370 A1 | 9/2014 | Sahin |
| 2015/0083772 A1 | 3/2015 | Miller et al. |
| 2015/0173763 A1 | 6/2015 | Liu |
| 2015/0209045 A1 | 7/2015 | Hodgkinson et al. |
| 2018/0338383 A1* | 11/2018 | Sgroi, Jr. ............... H01L 23/10 |
| 2019/0000538 A1* | 1/2019 | Widenhouse ...... A61B 18/1445 |
| 2019/0174636 A1* | 6/2019 | Sgroi, Jr. .......... B29C 45/14549 |
| 2019/0200981 A1* | 7/2019 | Harris ................... G16H 10/60 |

(56) References Cited

U.S. PATENT DOCUMENTS

| | | | | |
|---|---|---|---|---|
| 2019/0200998 | A1* | 7/2019 | Shelton, IV | A61M 1/73 |
| 2020/0146166 | A1* | 5/2020 | Sgroi, Jr. | H05K 3/287 |
| 2020/0214159 | A1* | 7/2020 | Sgroi, Jr. | A61B 17/00 |
| 2020/0315623 | A1* | 10/2020 | Eisinger | A61B 17/07207 |

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1671597 A1 | 6/2006 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3023077 A1 | 5/2016 |
| EP | 3398527 A1 | 11/2018 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 02080781 A2 | 10/2002 |
| WO | 2004047654 A2 | 6/2004 |
| WO | 2008107918 A1 | 9/2008 |
| WO | 2019130087 A1 | 7/2019 |

* cited by examiner

SURGICAL STAPLING DEVICE

CROSS-REFERENCE TO RELATED APPLICATION

This application claims the benefit of and priority to U.S. Provisional Patent Application No. 63/070,520, filed Aug. 26, 2020, the entire contents of which is incorporated by reference herein.

FIELD

This technology is generally related to surgical stapling devices and, more particularly, to surgical stapling devices with reusable adapter assemblies.

BACKGROUND

Surgical stapling devices for suturing tissue are well known in the art and typically include a handle assembly, an adapter assembly, and an end effector supported on the adapter assembly for treating tissue. Such stapling devices are capable of suturing tissue more quickly than traditional suturing techniques to reduce time required to perform surgical procedures and reduce trauma to a patient.

In order to reduce costs associated with surgical procedures that require tissue to be sutured, the end effector of the surgical stapling device may form part of a reload assembly that is releasably coupled to the adapter assembly and disposable to facilitate reuse of the handle assembly and the adapter assembly. In such devices, the adapter assembly and the reload assembly must undergo cleaning and sterilizing processes to facilitate reuse.

Typically, powered surgical stapling devices include electronics including electrical sensors to control operation of the stapling device. In addition, electrical connectors are provided between the adapter assembly and the handle assembly. In such devices, the electronics in the adapter assembly are sealed to prevent fluid ingress during use within a body cavity and during the cleaning and sterilizing processes.

In current devices, the adapter assembly includes a proximal portion that supports a plastic clam shell that is rotatably coupled to the handle assembly to facilitate rotation of the adapter assembly in relation to the handle assembly. The use of the plastic clam shell presents challenges when trying to seal the proximal portion of the adapter assembly during the cleaning and sterilization processes. In some situations, moisture may enter the proximal portion of the adapter assembly. This moisture may affect sterility of the adapter assembly and functionality of the electronics within the adapter assembly.

SUMMARY

In aspects, this disclosure is directed to an adapter assembly for a surgical device that includes an elongate body, a hub, a rotation knob, and at least one thermal energy storage member. The elongate body has a proximal portion and a distal portion adapted to releasably engage a reload assembly. The hub is supported on the proximal portion of the elongate body and is adapted to releasably engage a handle assembly. The rotation knob is rotatably fixed to the elongate body and is rotatably supported about the hub. The rotation knob is rotatable to rotate the elongate body in relation to the hub. The at least one thermal energy storage member is supported within the rotation knob and has a high heat capacity.

In other aspects, the disclosure is directed to a surgical device that includes a handle assembly, a housing, and at least one thermal energy storing device. The housing has a proximal portion and a distal portion, and the proximal portion is releasably coupled to the handle assembly. The at least one thermal energy storage member is supported by the housing and has a high heat capacity.

In other aspects, the disclosure is directed to a surgical stapling device including a handle assembly, an adapter assembly, and a reload assembly. The adapter assembly is releasably coupled to the handle assembly and includes an elongate body, a hub, a rotation knob, and at least one thermal energy storage member. The elongate body has a proximal portion and a distal portion. The hub is supported on the proximal portion of the elongate body and is releasably engaged with the handle assembly. The rotation knob is rotatably fixed to the elongate body and is rotatably supported about the hub. The rotation knob is rotatable to rotate the elongate body in relation to the hub. The at least one thermal energy storage member is supported within the rotation knob and has a high heat capacity. The reload assembly is releasably coupled to the distal portion of the elongate body.

In aspects of the disclosure, the at least one thermal energy storage member is formed from a sugar alcohol material.

In some aspects of the disclosure, the sugar alcohol material is selected from the group consisting of xylitol and erythritol.

In certain aspects of the disclosure, the sugar alcohol material is encapsulated in a material selected from the group consisting of plastic and steel.

In aspects of the disclosure, the rotation knob includes an internal surface that defines at least one cavity and the at least one thermal energy storage member is received within the at least one cavity.

In some aspects of the disclosure, the at least one thermal energy storage member includes a plurality of thermal storage members and the at least one cavity includes a plurality of cavities.

In certain aspects of the disclosure, the adapter assembly includes an anvil retainer that projects from the distal portion of the elongate body and is movable between advanced and retracted positions.

In aspects of the disclosure, the surgical stapling device includes an anvil assembly that is releasably supported on the anvil retainer of the adapter assembly.

In aspects of the disclosure, the reload assembly includes a staple cartridge.

Other features of the disclosure will be appreciated from the following description.

BRIEF DESCRIPTION OF DRAWINGS

Various aspects of the disclosure are described herein below with reference to the drawings, wherein.

DETAILED DESCRIPTION

The disclosed surgical device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, and similar terms are used to assist in understanding the description and are not intended to limit the disclosure.

In this description, the term "proximal" is used generally to refer to that portion of the device that is closer to a clinician during customary usage of the device, while the term "distal" is used generally to refer to that portion of the device that is farther from the clinician during customary usage of the device. In addition, the term "endoscopic" is used generally used to refer to endoscopic, laparoscopic, arthroscopic, and/or any other procedure conducted through a small diameter incision or cannula. Further, the term "clinician" is used generally to refer to medical personnel including doctors, nurses, and support personnel.

This disclosure is directed to a reusable surgical device that requires sterilization and cleaning prior to reuse and includes an internal cavity that may retain water. The surgical device includes a body or housing that supports one or more thermal energy storage members that retain or store heat during a cleaning and sterilization process. The stored heat functions to evaporate any water that remains within the housing of the surgical device after the cleaning and sterilization process is completed to minimize any likelihood of infection of a patient or damage to electronics within the surgical device that may result or occur due to the presence of the water within the surgical device.

Figure 1:
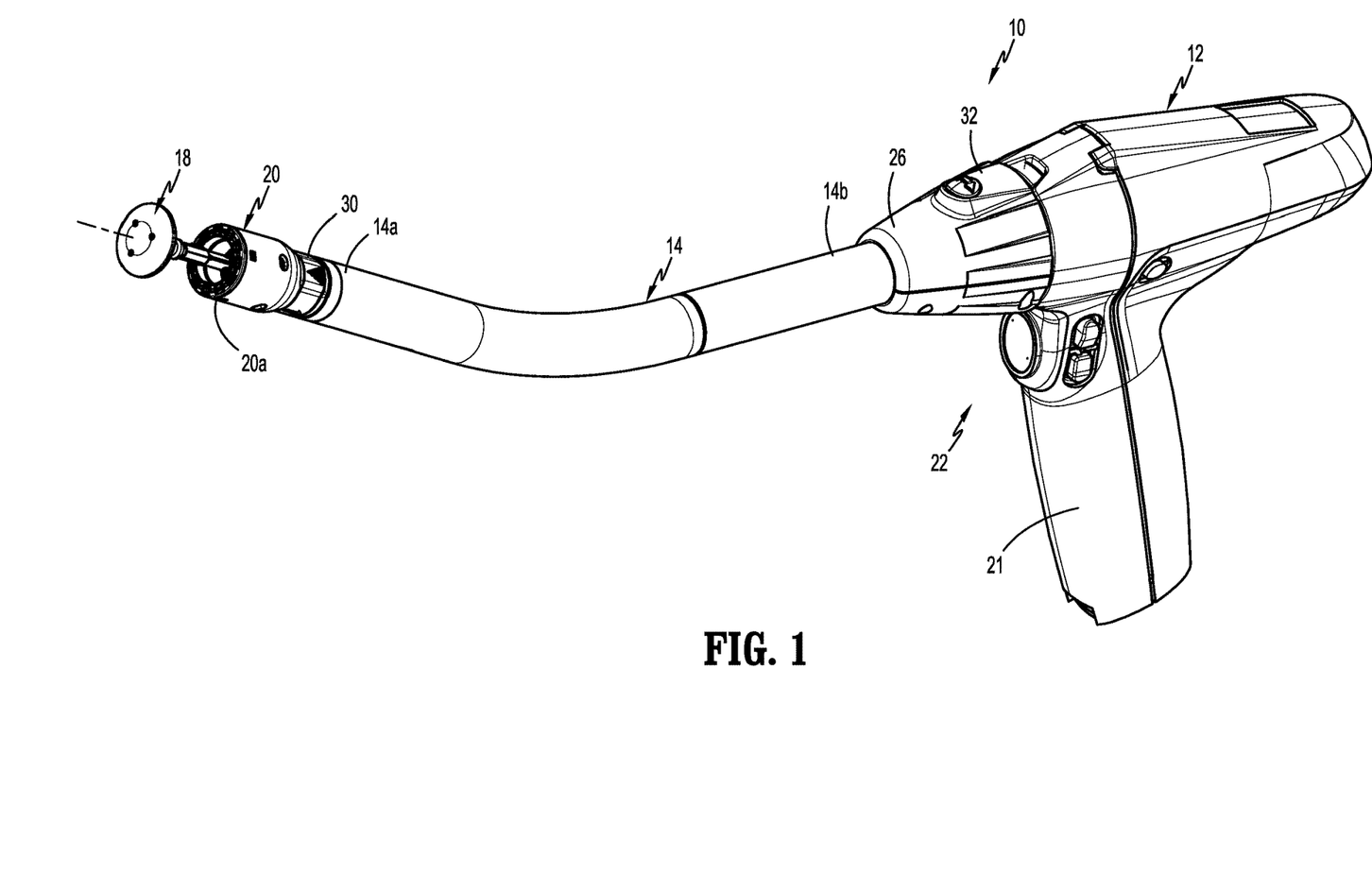
FIG. 1 is a side perspective view of a surgical stapling device including aspects of the disclosure.

FIG. 1 illustrates a surgical device including aspects of the disclosure shown generally as stapling device 10. The stapling device 10 includes a handle assembly 12, an adapter assembly 14, an anvil assembly 18, and a reload assembly 20. The reload assembly 20 includes a staple cartridge 20a that supports a plurality of staples (not shown). The handle assembly 12 includes a stationary grip 21 that supports actuation buttons 22 for controlling operation of various functions of the stapling device 10 including approximation of the anvil and reload assemblies 18 and 20, respectively, firing of staples from the reload assembly 20, and cutting or coring of tissue. The adapter assembly 14 includes an anvil retainer 24 (FIG. 2) and is coupled to the handle assembly 12 by a clam shell or rotation knob 26. The rotation knob 26 is rotatably supported between portions of the adapter assembly 14 to facilitate rotation of the adapter assembly 14 and the reload assembly 20 in relation to the handle assembly 12. The anvil assembly 18 is removably supported on the anvil retainer 24 (FIG. 2) of the adapter assembly 14 and is movable in relation to the reload assembly 20 between open and clamped positions. The reload assembly 20 includes a proximal portion 30 that is releasably coupled to a distal portion 14a of the adapter assembly 14 to facilitate removal and replacement of a spent or fired reload assembly 20 from the adapter assembly 14. The rotation knob 26 of the adapter assembly 14 includes a release button 32 that is operable to facilitate rotation of the adapter assembly 14 in relation the handle assembly 12. The adapter assembly 14 and handle assembly 12 are separable from each other to facilitate cleaning and sterilization of each of these components.

The stapling device 10 is illustrated as an electrically powered stapling device and includes an electrically powered handle assembly 12. In aspects of the disclosure, the stationary handle 20 of the handle assembly 12 supports a battery pack or one or more batteries (not shown) that provide power to the stapling device 10. The adapter assembly 14 translates power from the handle assembly 12 to the reload assembly 20 and to the anvil assembly 18 to actuate the reload assembly 20. Examples of electrically powered stapling devices can be found in U.S. Pat. Nos. 9,055,943, 9,023,014, and U.S. Publication Nos. 2018/0125495, and 2017/0340351.

Alternately, it is envisioned that aspects of the disclosure could also be incorporated into a manually powered stapling device such as disclosed in U.S. Pat. No. 7,303,106 or a stapling device that is configured for use with a robotic system such as disclosed in U.S. Pat. No. 9,962,159 that does not include a handle assembly.

Figure 2:
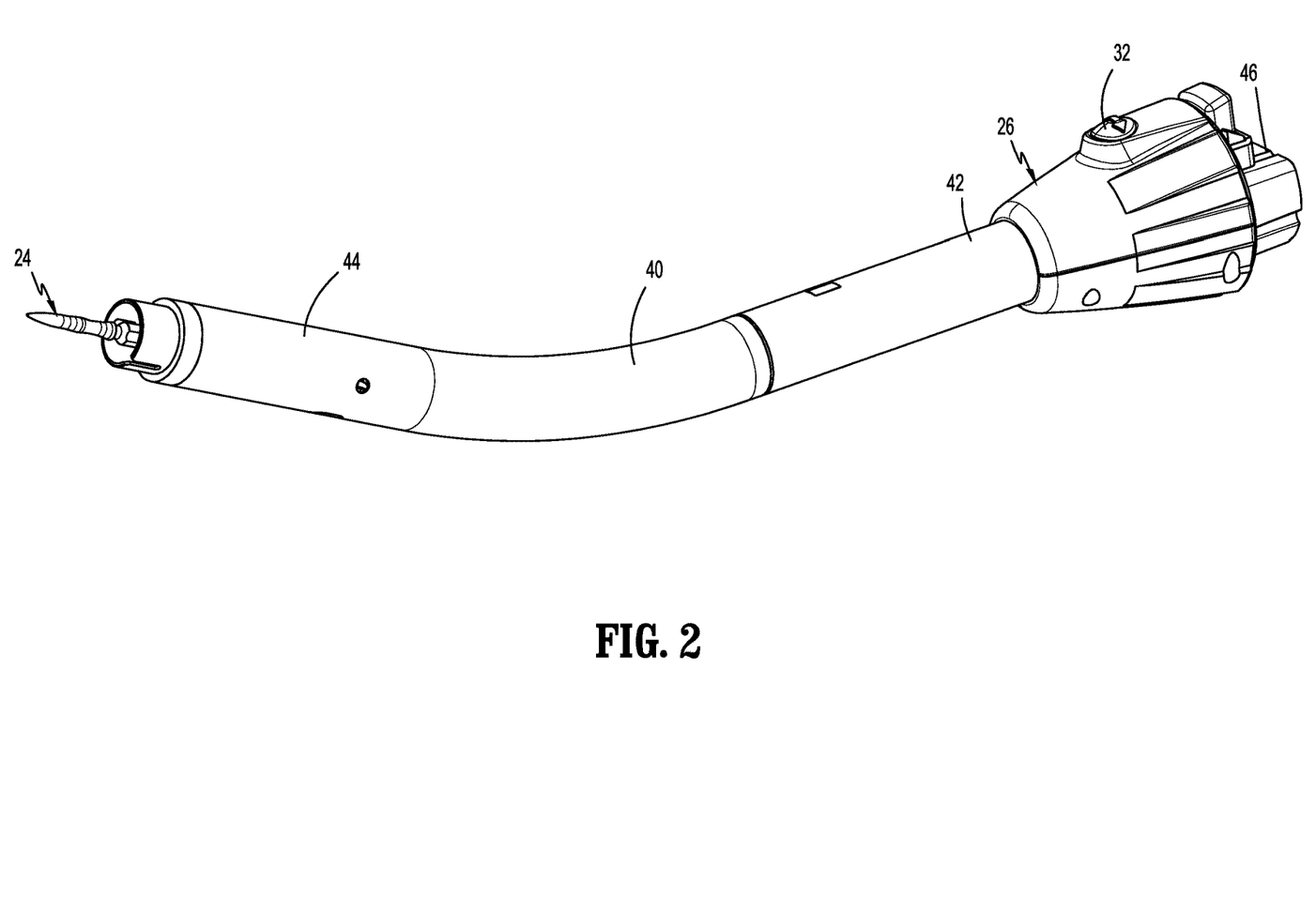
FIG. 2 is a side perspective view of an adapter assembly of the surgical stapling device shown in FIG. 1.

FIG. 2 illustrates the adapter assembly 14 which includes an elongate housing or body 40 having a proximal portion 42 and a distal portion 44. The distal portion 44 of the elongate body 40 is adapted to releasably engage the proximal portion 30 of the reload assembly 20 and receives the anvil retainer 24. The proximal portion 44 of the elongate body 40 supports a hub 46 that is fixedly coupled to the handle assembly 12. The rotation knob 26 is rotatably mounted about the hub 46 and is fixedly secured to the elongate body 40 to facilitate rotation of the elongate body 40 of the adapter assembly 14 in relation to the hub 46 and the handle assembly 12 (FIG. 1).

Figure 3:
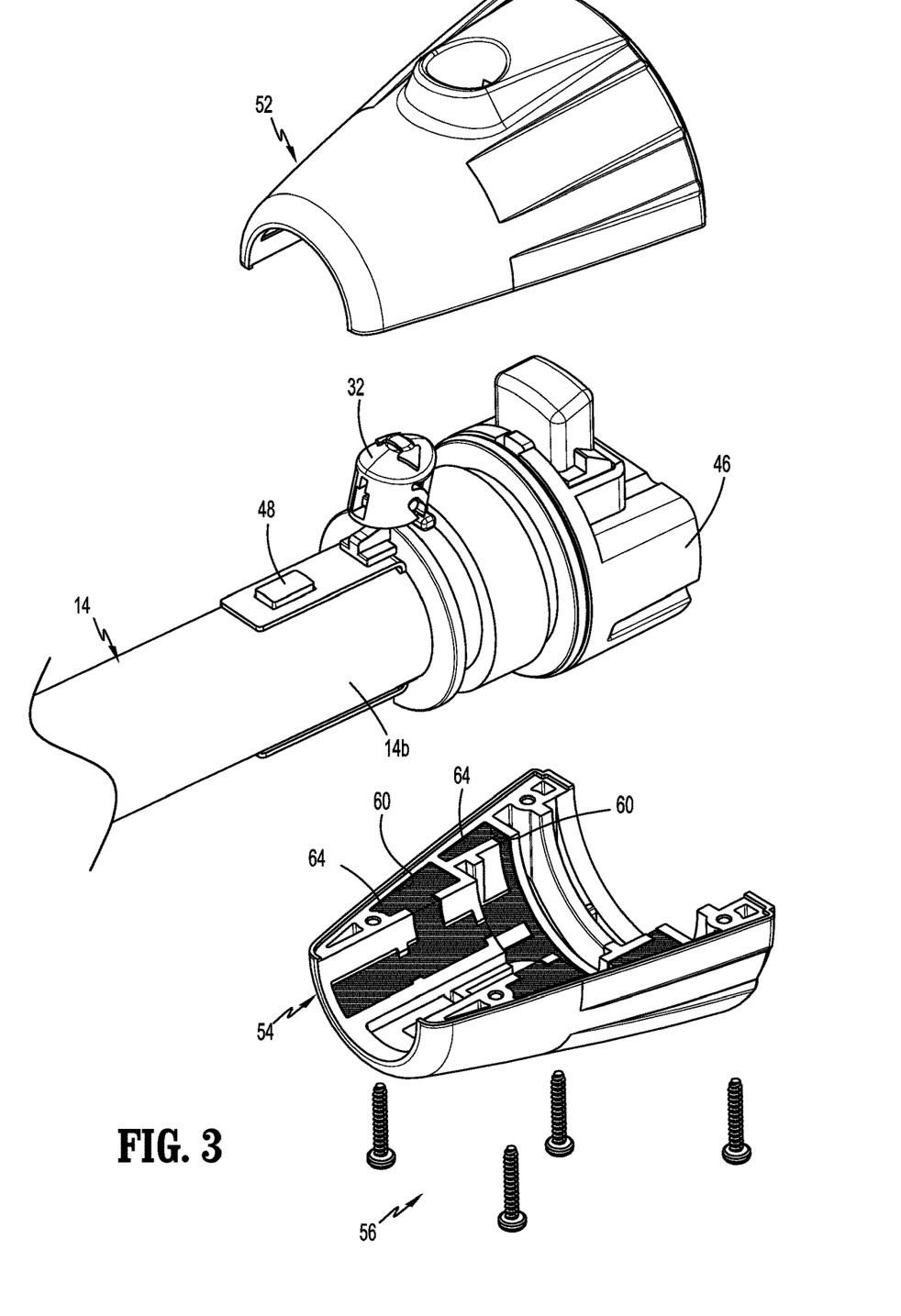
FIG. 3 is a side perspective view of a proximal portion of the adapter assembly shown in FIG. 2 with first and second half-sections of a rotation knob of the adapter assembly separated from remaining portion of the adapter assembly.

FIG. 3 illustrates the proximal portion 14b (FIG. 1) of the adapter assembly 14 including the proximal portion 42 of the elongate body 40, the rotation knob 36, and the hub 46. The proximal portion 42 of the elongate body 40 supports diametrically opposed protrusions 48 that extend radially outward from an outer surface of the elongate body 40. The protrusions 48 are received within recesses 50 defined within the rotation knob 26 to rotatably fix the rotation knob 26 to the elongate body 40 of the adapter assembly 14.

Figure 4:
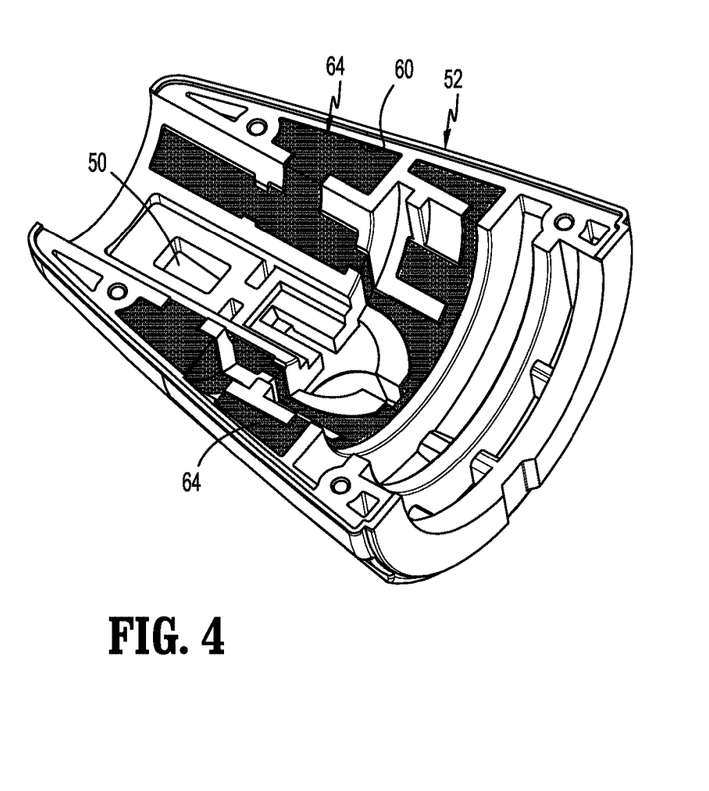
FIG. 4 is a perspective view of the first half-section of the rotation knob with thermal energy storage members positioned within recesses of the first half-section.
Figure 5:
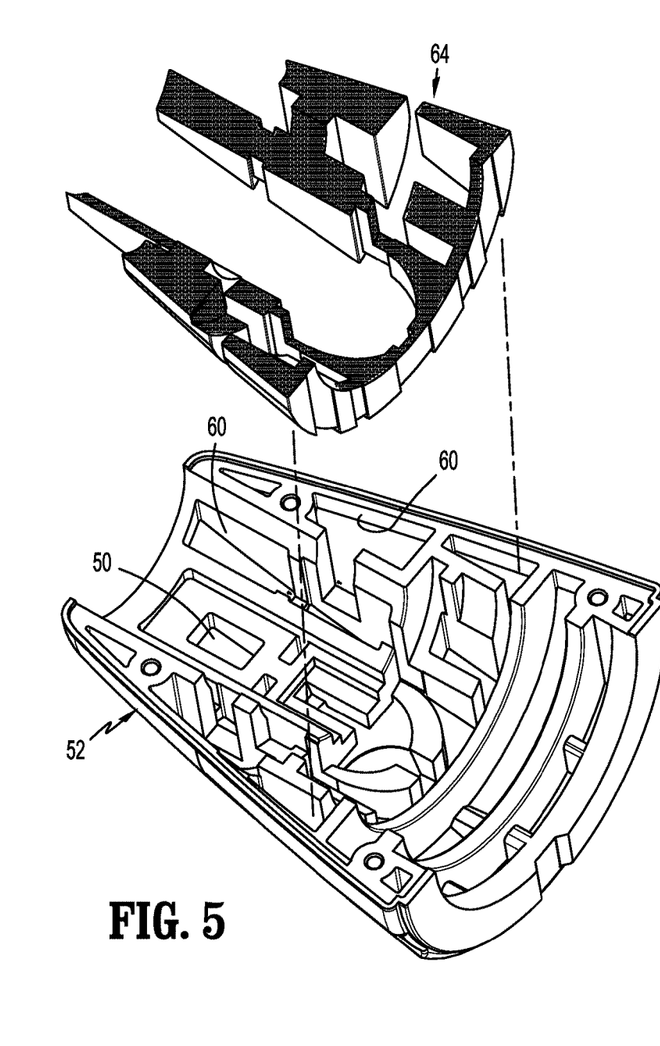
FIG. 5 is a side perspective view of the first half-section of the rotation knob shown in FIG. 4 with the thermal storage members separated from the first half-section.
Figure 6:
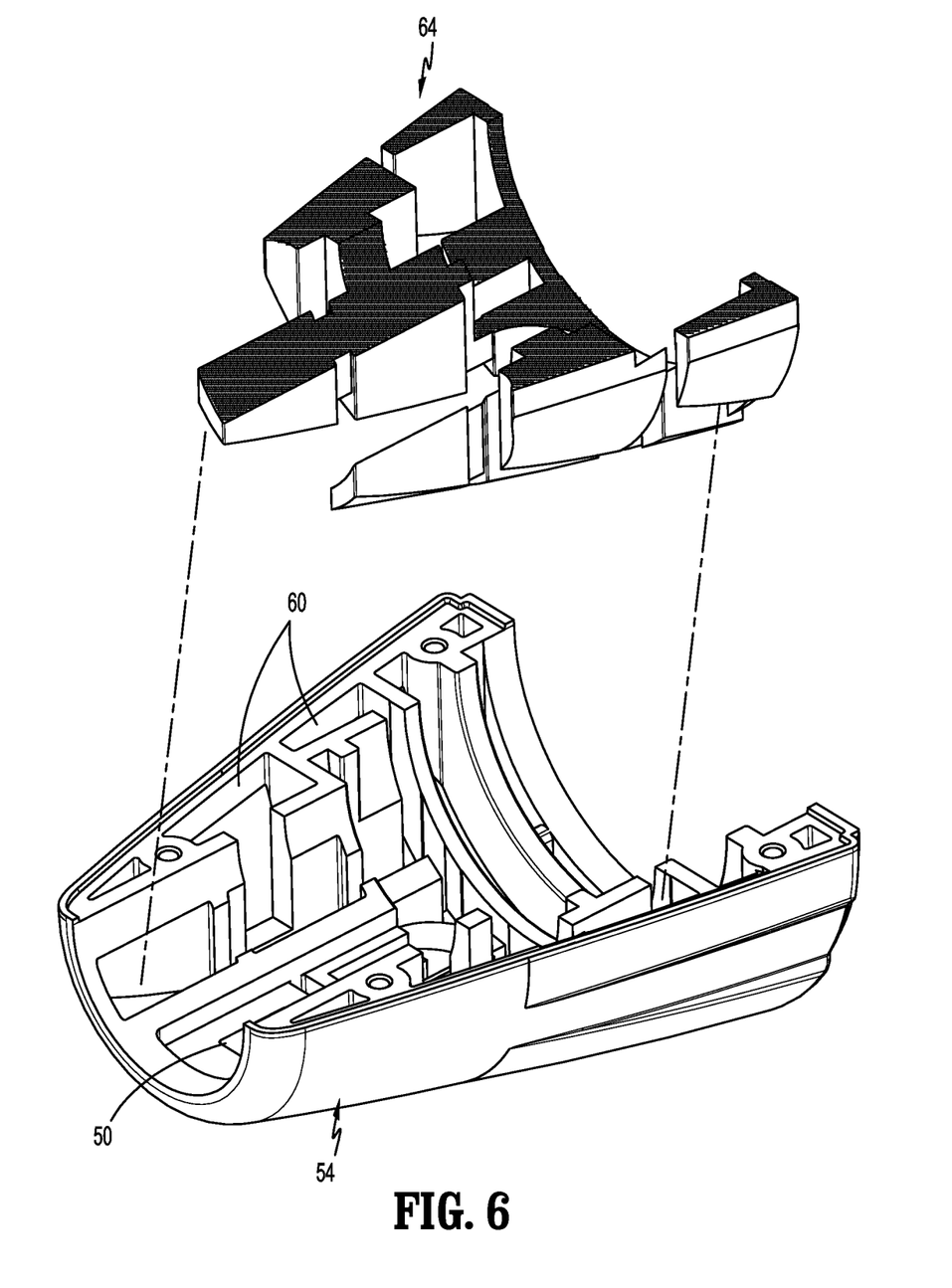
FIG. 6 is a side perspective view of the second half-section of the rotation knob shown in FIG. 4 with the thermal storage members separated from the second half-section.

FIGS. 4-6 illustrate the rotation knob 26 which includes a first half-section 52 and a second half-section 54. The first and second half-sections 52 and 54 are coupled together about the proximal portion 14b of the elongate body 40 of the adapter assembly 14 and the hub 46 of the adapter assembly 14. In aspects of the disclosure, the first and second half-sections 52 and 54 are coupled together with screws 56. Alternately, other coupling devices or techniques can be used to couple the first and second half-sections 52 and 54, respectively, together, e.g., adhesives, welding, interlocking structure, etc. Each of the first and second half-sections 52 and 54, respectively, defines one of the recesses 50 that receives one of the protrusions 48 on the elongate body 40 of the adapter assembly 14 to rotatably fix the rotation knob 26 to the proximal portion 14b of the adapter assembly 14. Each of the first and second half-sections 52 and 54 includes an inner surface that defines one or more cavities 60.

In aspects of the disclosure, the rotation knob 26 supports one or more thermal energy storage members 64. In certain aspects of the disclosure, the thermal energy storage members 64 are received within the one or more of the cavities 60 defined within the first and second half-sections 52 and 54, respectively, of the rotation knob 26. Alternately, the thermal energy storage members 64 can be supported anywhere in the adapter assembly 14 where moisture is likely to collect. Locating the energy storage members 64 within the cavities 60 of the rotation knob 26 provides the additional advantage of occupying space wherein water is likely to collect.

In aspects of the disclosure, the thermal energy storage members 60 are formed of a material having a high heat capacity that can store heat through both sensible and latent heat capacities such as a sugar alcohol, e.g., xylitol or erythritol, which have melting temperatures near that of boiling water. As used herein "high heat capacity" means a material that has a heat capacity similar to or greater than that of water. In certain aspects of the disclosure, the material is encapsulated in a material that does not melt during cleaning and sterilizing of the adapter assembly 14, e.g., plastic or steel. Alternately, the thermal energy storage members 64 can be formed entirely of steel or other metal that has a high heat capacity.

During a sterilizing and cleaning process, e.g., autoclaving process, the surgical device being cleaned and sterilized, e.g., the adapter assembly 14, is heated until it reaches an equilibrium temperature. The surgical device is then dried for a fixed amount of time without further heat input. Due to the thermodynamic cooling effect of evaporation, the surgical device may cool beyond its ability to evaporate water trapped within the surgical device. By adding thermal energy storage devices within the body or housing of the surgical device, specifically within areas that most commonly retain water, enough thermal energy can remain within the housing of the surgical device to evaporate all the water remaining within the housing of the surgical device.

Although this disclosure is directed to a circular stapling device, and more particularly to an adapter assembly of a surgical stapling device, it is envisioned that the benefits of providing one or more thermal energy storage devices within a body or housing of a surgical device that requires sterilization and cleaning would be applicable to all surgical instruments having internal cavities that require sterilization and cleaning.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. An adapter assembly for a surgical device comprising:
   an elongate body having a proximal portion and a distal portion, the distal portion adapted to releasably engage a reload assembly;
   a hub supported on the proximal portion of the elongate body, the hub adapted to releasably engage a handle assembly;
   a rotation knob rotatably fixed to the elongate body and rotatably supported about the hub, the rotation knob being rotatable to rotate the elongate body in relation to the hub; and
   at least one thermal energy storage member supported within the rotation knob, the at least one thermal member having a high heat capacity.

2. The adapter assembly of claim 1, wherein the at least one thermal energy storage member is formed from a sugar alcohol material.

3. The adapter assembly of claim 2, wherein the sugar alcohol material is selected from the group consisting of xylitol and erythritol.

4. The adapter assembly of claim 3, wherein the sugar alcohol material is encapsulated in a material selected from the group consisting of plastic and steel.

5. The adapter assembly of claim 1, wherein the rotation knob includes an internal surface that defines at least one cavity and the at least one thermal energy storage member is received within the at least one cavity.

6. The adapter assembly of claim 5, wherein the at least one thermal energy storage member includes a plurality of thermal storage members and the at least one cavity includes a plurality of cavities.

7. The adapter assembly of claim 1, wherein the adapter assembly includes an anvil retainer, the anvil retainer projecting from the distal portion of the elongate body and being movable between advanced and retracted positions.

8. A surgical stapling device comprising:
   a handle assembly;
   an adapter assembly releasably coupled to the handle assembly, the adapter assembly including:
     an elongate body having a proximal portion and a distal portion;
     a hub supported on the proximal portion of the elongate body, the hub releasably engaged with the handle assembly;
     a rotation knob rotatably fixed to the elongate body and rotatably supported about the hub, the rotation knob being rotatable to rotate the elongate body in relation to the hub; and
     at least one thermal energy storage member supported within the rotation knob, the at least one thermal member having a high heat capacity; and
   a reload assembly releasably coupled to the distal portion of the elongate body.

9. The surgical stapling device of claim 8, wherein the at least one thermal energy storage member is formed from a sugar alcohol material.

10. The surgical stapling device of claim 9, wherein the sugar alcohol material is selected from the group consisting of xylitol and erythritol.

11. The surgical stapling device of claim 9, wherein the sugar alcohol material is encapsulated in a material selected from the group consisting of plastic and steel.

12. The surgical stapling device of claim 8, wherein the rotation knob includes an internal surface that defines at least one cavity and the at least one thermal energy storage member is received within the at least one cavity.

13. The surgical stapling device of claim 12, wherein the at least one thermal energy storage member includes a plurality of thermal storage members and the at least one cavity includes a plurality of cavities.

14. The surgical stapling device of claim 8, wherein the adapter assembly includes an anvil retainer, the anvil retainer projecting from the distal portion of the elongate body and being movable between advanced and retracted positions.

15. The surgical stapling device of claim 14, further including an anvil assembly, the anvil assembly being releasably supported on the anvil retainer of the adapter assembly.

16. The surgical stapling device of claim 8, wherein the reload assembly includes a staple cartridge.

17. A surgical device comprising:
a handle assembly;
a housing having a proximal portion and a distal portion, the proximal portion being releasably coupled to the handle assembly; and
at least one thermal energy storage member supported by the housing, the at least one thermal member having a high heat capacity.

18. The surgical device of claim 17, further including a reload assembly releasably coupled to the distal portion of the housing.

19. The surgical device of claim 17, further including a rotation knob, the rotation knob being rotatably fixed to the housing and rotatable in relation to the handle assembly such that rotation of the rotatable knob rotates the housing in relation to the handle assembly.

20. The surgical device of claim 19, wherein the at least one thermal energy source is supported within the rotation knob.

* * * * *